(12) United States Patent
Kusuura

(10) Patent No.: US 9,080,138 B2
(45) Date of Patent: Jul. 14, 2015

(54) CELL CULTURE SYSTEM, CELL CULTURE METHOD, CELL CULTURE VESSEL AND METHOD FOR MANUFACTURING CELL CULTURE VESSEL

(75) Inventor: Takahisa Kusuura, Kawasaki (JP)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 940 days.

(21) Appl. No.: 12/665,020

(22) PCT Filed: Jan. 29, 2009

(86) PCT No.: PCT/JP2009/051428
§ 371 (c)(1),
(2), (4) Date: Dec. 16, 2009

(87) PCT Pub. No.: WO2010/086976
PCT Pub. Date: Aug. 5, 2010

(65) Prior Publication Data
US 2011/0104729 A1    May 5, 2011

(51) Int. Cl.
*C12M 3/00* (2006.01)
*C12M 1/00* (2006.01)
*C12M 1/42* (2006.01)
*C12M 1/34* (2006.01)

(52) U.S. Cl.
CPC ........... *C12M 21/02* (2013.01); *C12M 23/20* (2013.01); *C12M 23/22* (2013.01); *C12M 35/08* (2013.01); *C12M 41/06* (2013.01); *C12M 41/46* (2013.01)

(58) Field of Classification Search
CPC ...... C12M 21/02; C12M 23/20; C12M 23/22; C12M 31/00; C12M 31/02; C12M 35/08; C12M 41/06; C12M 41/46; C12N 13/00; C12N 2529/10; C12N 2533/10; C12N 2537/00; C12N 2539/00
USPC ............... 435/30, 173.8, 402, 286.1, 288.7, 3
See application file for complete search history.

(56) References Cited

U.S. PATENT DOCUMENTS

| 6,914,637 | B1 | 7/2005 | Wolf et al. |
| 7,687,251 | B2 | 3/2010 | Hattori et al. |
| 2005/0279730 | A1 | 12/2005 | Miyake et al. |
| 2006/0233854 | A1* | 10/2006 | Seliktar et al. ................. 424/422 |
| 2007/0122901 | A1* | 5/2007 | Morita et al. ................. 435/325 |

(Continued)

FOREIGN PATENT DOCUMENTS

| EP | 1 686 171 A1 | 8/2006 |
| JP | 63-196273 | 8/1988 |

(Continued)

OTHER PUBLICATIONS

Copy of Notice of Reasons for Rejection for JP 2009-541659 mailed Apr. 13, 2010 (with English translation).

(Continued)

*Primary Examiner* — William H Beisner
(74) *Attorney, Agent, or Firm* — Foley & Lardner LLP

(57) ABSTRACT

A cell culture system comprising a light source for emitting light, a light intensity regulator for regulating the light intensity of the light emitted by the light source, a cell activity-measuring device for measuring the activity of cells cultured on a photocatalytic film irradiated with the light, and an association device for associating the light intensity with the cell activity.

7 Claims, 7 Drawing Sheets

(56) References Cited

U.S. PATENT DOCUMENTS

2007/0141697 A1* 6/2007 Hattori et al. ............ 435/289.1
2007/0243613 A1 10/2007 Miyake et al.

FOREIGN PATENT DOCUMENTS

| | | |
|---|---|---|
| JP | 01-141588 | 6/1989 |
| JP | 2002253204 A * | 9/2002 |
| JP | 2005-514873 A | 5/2005 |
| JP | 2005-261432 | 9/2005 |
| JP | 2008-132126 | 6/2008 |
| WO | WO 2005/038011 | 4/2005 |
| WO | WO 2005/093039 | 10/2005 |

OTHER PUBLICATIONS

Office Action issued in Japanese Appl. No. 2009-541659 mailed Dec. 11, 2009 (with English translation).

Okochi, Norihiko et al., "Transfer Printing of Micropatterned Endothelial Cells," Membrane, vol. 32, No. 5, 2007, pp. 281-286 (with English translation).

Sawase, T. et al., "Enhancement of cell attachment and proliferation on photo-induced hydrophilic anodized titanium," Japanese Journal of Oral Implantology, vol. 20, No. 1, 2007, pp. 81-82 (with English translation).

Liu, C. et al., "The Interferon-inducible p204 Protein Acts as a Transcriptional Coactivator of Cbfal and Enhances Osteoblast Differentiation," *Journal of Biological Chemistry*, vol. 280, No. 4, 2005, pp. 2788-2796.

International Search Report and Written Opinion received for PCT/JP2009/051428 dated Aug. 18, 2011 (10 pages).

International Search Report and Written Opinion received for PCT/JP2009/051428 dated Mar. 24, 2009.

* cited by examiner

FIG. 2

| LIGHT INTENSITY | PROLIFERATION RATE OF CELLS |
|---|---|
| $V_1$ | $A_1$ |
| $V_2$ | $A_2$ |
| $V_3$ | $A_3$ |
| | |
| | |
| | |
| | |
| | |
| | |
| $V_n$ | $A_n$ |

FIG. 6

| COMPOSITION OF PHOTOCATALYTIC FILM | PROLIFERATION RATE OF CELLS |
|---|---|
| $C_1$ | $A_1$ |
| $C_2$ | $A_2$ |
| $C_3$ | $A_3$ |

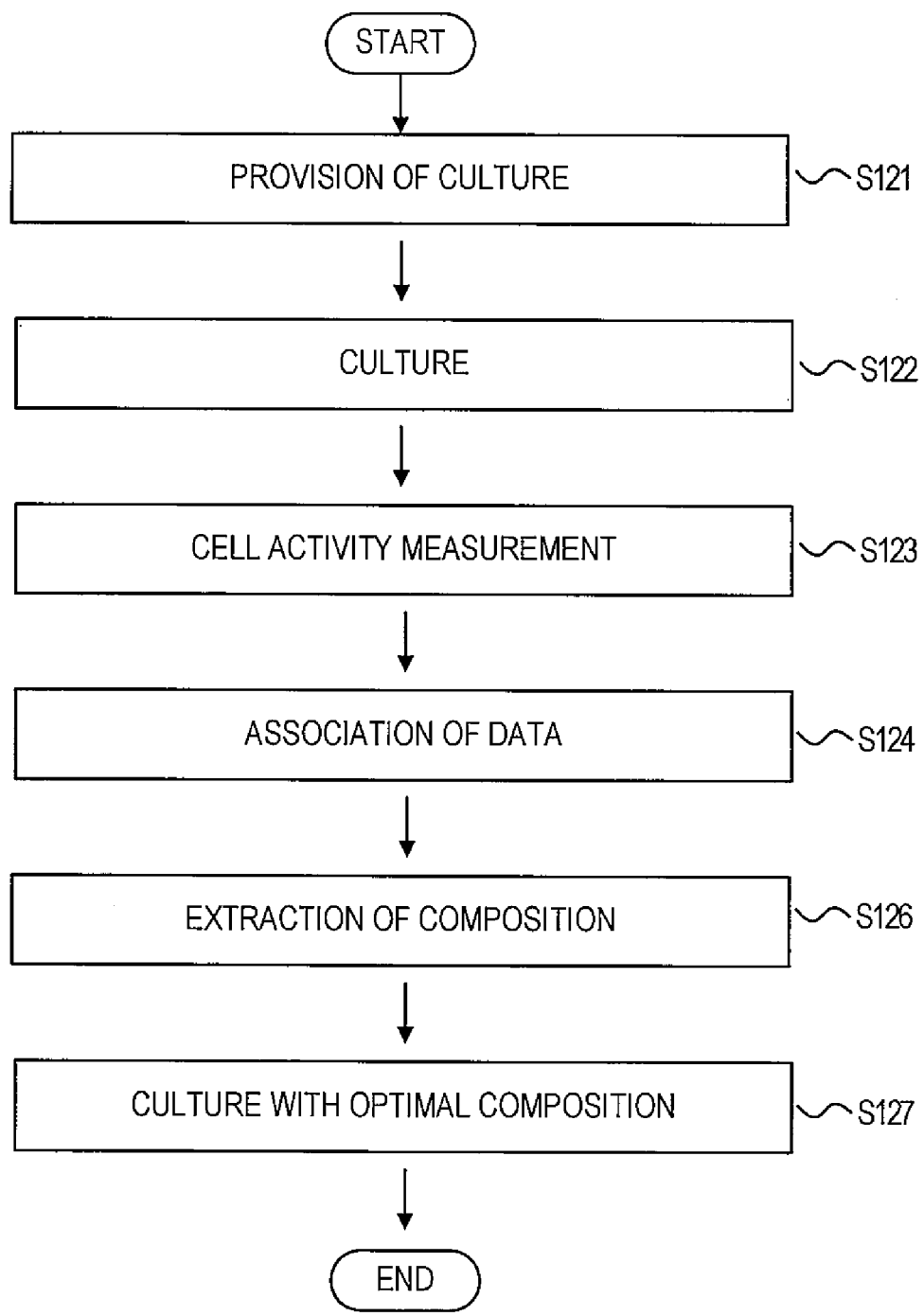

CELL CULTURE SYSTEM, CELL CULTURE METHOD, CELL CULTURE VESSEL AND METHOD FOR MANUFACTURING CELL CULTURE VESSEL

CROSS-REFERENCE TO RELATED APPLICATIONS

The present application is a U.S. national stage application claiming the benefit of International Application No. PCT/JP2009/051428, filed on Jan. 29, 2009, the entire contents of which is incorporated herein by reference in its entirety.

TECHNICAL FIELD

The technology described relates to cell culture technologies and in particular, to a cell culture system, a cell culture method, a cell culture vessel and a method for manufacturing the cell culture vessel.

BACKGROUND ART

Large-scale culture of cells is sometimes required in manufacturing biological agents including antiviral agents such as vaccine and interferon or hormones. Most cells utilized in the production of biological active substances used for making biological agents have adhesive properties to a scaffold material. Thus, there is a need for a proposal of method for efficiently and extensively culturing cells having adhesive properties to the scaffold material. Here, the adhesive properties of cells to the scaffold material have been shown to be related to activities of the cells represented by a growth rate and the like (see Japanese Patent Laid-Open Nos. 63-196273 and 01-141588).

DISCLOSURE OF THE INVENTION

Problems to be Solved by the Invention

However, there has previously been no technique for searching suitable culture conditions for cells through controlling adhesive properties of the cells to the scaffold material. Accordingly, it is desired to provide a cell culture system, a cell culture method, a cell culture vessel and a method for manufacturing the cell culture vessel which enable easy search of suitable culture conditions through controlling adhesive properties of cells to a scaffold material.

Means for Solving the Problems

According to an aspect of the present disclosure, a cell culture system is provided which comprises a light source for emitting light, a light intensity regulator for regulating the light intensity of the light emitted by the light source, a cell activity-measuring device for measuring the activity of cells cultured on a photocatalytic film irradiated with the light or on each of a plurality of photocatalytic films of differing compositions, an association device for associating the light intensity or the composition of each of the plurality of photocatalytic films with the cell activity, an information storage device for storing information about the activity of the cells on the photocatalytic film associated with the light intensity, and an extraction device for extracting a value of the light intensity that maximizing the cell activity, wherein the light source irradiates the photocatalytic film with light having the light intensity of the extracted value and wherein the cell activity-measuring device measures the proliferation rate, growth rate, amount of secreted material or gene expression level of the cells.

According to an aspect of the present disclosure, a cell culture system is also provided which comprises a light source for emitting light, a light intensity regulator for regulating the light intensity of the light emitted by the light source, a cell activity-measuring device for measuring the activity of cells cultured on a photocatalytic film irradiated with the light, and an association device for associating the light intensity with the cell activity.

According to an aspect of the present disclosure, a cell culture method is further provided which comprises emitting light of which light intensity can be regulated, measuring the activity of cells cultured on a photocatalytic film irradiated with the light, and associating the light intensity with the cell activity.

According to an aspect of the present disclosure, a cell culture system is also provided which comprises a cell activity-measuring device for measuring the activity of cells cultured on each of a plurality of photocatalytic films of differing compositions and an association device for associating the composition of each of the plurality of photocatalytic films with the cell activity.

According to an aspect of the present disclosure, a cell culture method is further provided which comprises measuring the activity of cells cultured on each of a plurality of photocatalytic films of differing compositions and associating the composition of each of the plurality of photocatalytic films with the cell activity.

According to an aspect of the present disclosure, a cell culture vessel is also provided which comprises a substrate and a photocatalytic film disposed on the substrate.

According to an aspect of the present disclosure, a method for manufacturing a cell culture vessel is further provided which comprises measuring the activity of cells cultured on each of a plurality of photocatalytic films of differing compositions, associating the composition of each of the plurality of photocatalytic films with the cell activity, extracting a composition that maximizing the cell activity from the compositions of the plurality of photocatalytic films, and forming a photocatalytic film consisting of the extracted composition on a substrate.

According to an aspect of the present disclosure, a method for producing cells is also provided which comprises emitting light of which light intensity can be regulated, measuring the activity of cells cultured on a photocatalytic film irradiated with the light, and associating the light intensity with the cell activity.

According to an aspect of the present disclosure, a method for producing cells is further provided which comprises measuring the activity of cells cultured on each of a plurality of photocatalytic films of differing compositions and associating the composition of each of the plurality of photocatalytic films with the cell activity.

According to an aspect of the present disclosure, cells are also provided which are produced by a method comprising emitting light of which light intensity can be regulated, measuring the activity of cells cultured on a photocatalytic film irradiated with the light, and associating the light intensity with the cell activity.

According to an aspect of the present disclosure, cells are further provided which are produced by a method comprising measuring the activity of cells cultured on each of a plurality of photocatalytic films of differing compositions and associating the composition of each of the plurality of photocatalytic films with the cell activity.

BRIEF DESCRIPTION OF THE DRAWINGS

FIG. 2 is a table of the data on the proliferation rate associated with the data on the light intensity according to the first embodiment;

FIG. 6 is a table of the data on the proliferation rate associated with the data on the composition of the photocatalytic film according to the third embodiment; and FIG. 7 is a flow chart depicting the cell culture method according to the third embodiment.

BEST MODE FOR CARRYING OUT THE INVENTION

Figure 1:
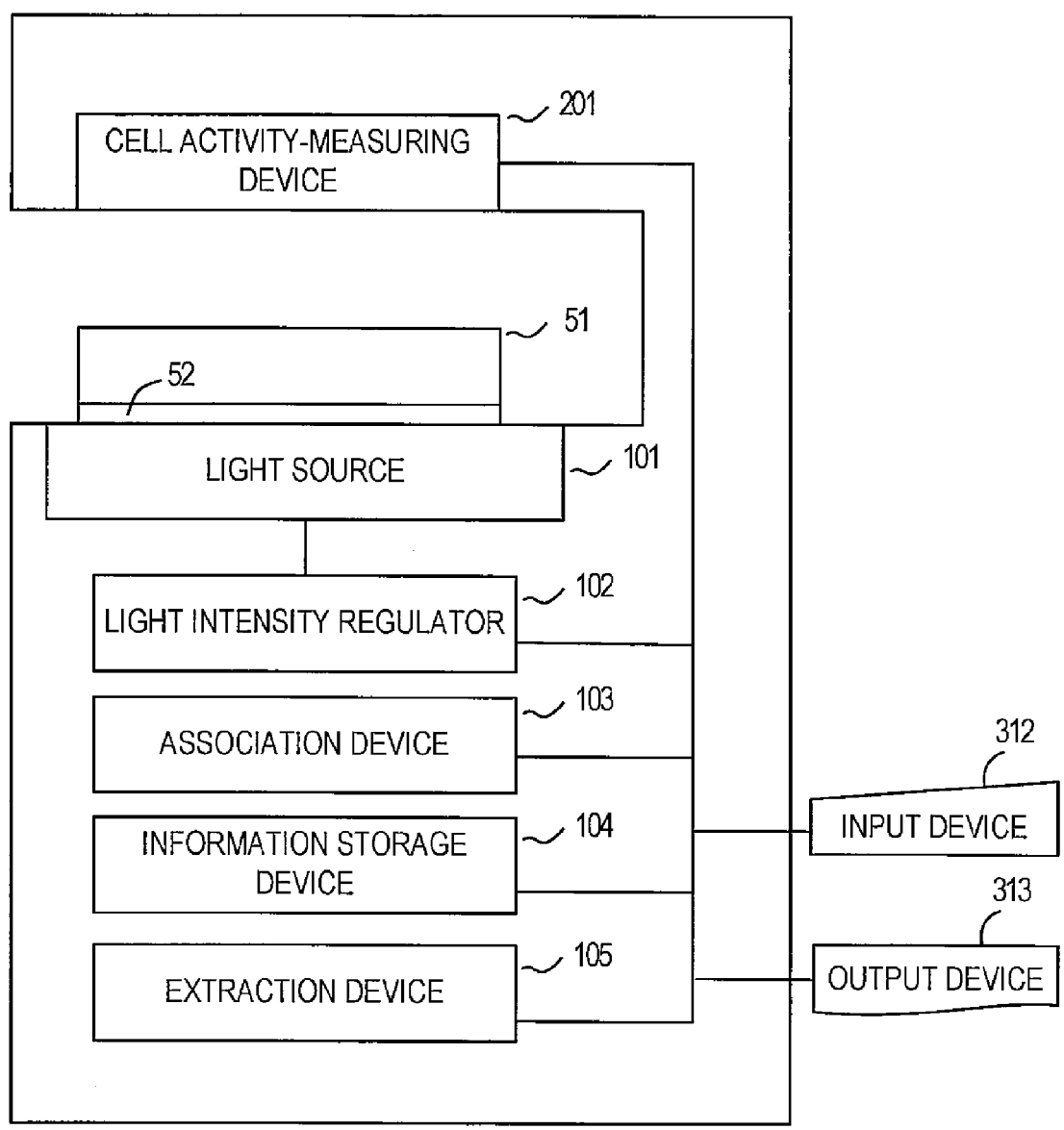
FIG. 1 is a schematic diagram of the cell culture system according to the first embodiment.

Embodiments of the present disclosure is described below. In the description of the following drawings, the same or similar parts are denoted by the same or similar reference numerals. However, the drawings are schematic. Thus, specific dimensions and the like should be determined in light of the following description. Naturally, portions of which relations or proportions of dimensions are relatively different among the drawings are included.

(First Embodiment)

The cell culture system shown in FIG. 1 according to a first embodiment comprises a light source 101 for emitting light, a light intensity regulator 102 for regulating the light intensity of the light emitted by the light source 101, a cell activity-measuring device 201 for measuring the activity of cells cultured on a photocatalytic film 52 irradiated with the light, and an association device 103 for associating the light intensity with the cell activity.

The light source 101 emits ultraviolet light or visible light. The light source 101 which can be used is, for example, black light, a fluorescent discharge tube, a low-pressure mercury lamp, a xenon lamp capable of emitting a continuous spectrum from the ultraviolet to infrared region (180 nm to 2,000 nm), a light emitting diode, a superluminescent diode, or a semiconductor laser. The light intensity regulator 102 regulates electric power supplied to the light source 101 to regulate the light intensity of the light emitted by the light source 101.

A cell culture vessel 51 such as a petri dish is disposed over the light source 101. The cell culture vessel 51 is composed of a transparent material such as an acrylic resin and silicon oxide ($SiO_2$). The photocatalytic film 52 is disposed on the transparent bottom face of the cell culture vessel 51 and contains titanium oxide ($TiO_2$) and the like as the composition. The thickness of the photocatalytic film 52 is, for example, 30 nm to 500 nm.

Methods for forming the photocatalytic film 52 on the bottom face of the cell culture vessel 51 include a method which involves coating a solution of titanium alkoxide, a titanium organic acid or titanium peroxide as a precursor of titanium oxide or of a titanium salt such as titanium chloride on the bottom face of the cell culture vessel 51, followed by heat treatment. In the case where the solution is coated, a dip-coating method, a spin coat method, a roll coat method, a bar coat method, a spray coat method, a screen printing method, or the like can be used. The temperature for the heat treatment is, for example, 100° C. to 700° C.

Methods for forming the photocatalytic film 52 on the bottom face of the cell culture vessel 51 also include a method which involves coating on the bottom face of the cell culture vessel 51 a solution in which a binder component is mixed with titanium oxide powder or a sol having titanium oxide powder dispersed in a solvent, followed by drying or sintering. In addition, the photocatalytic film 52 may be formed on the bottom face of the cell culture vessel 51 by adding organic polymer beads to a solution containing a photocatalyst such as titanium oxide, which is then coated on the bottom face of the cell culture vessel 51, followed by sintering the solution. The addition of the organic polymer beads inhibits the heat shrink of the photocatalytic film 52 during the sintering.

The cell culture vessel 51 in which the photocatalytic film 52 has been formed is filled with a culture medium, and cells are cultured on the photocatalytic film 52. The photocatalytic film 52 is irradiated with light emitted from the light source 101. When light is irradiated from the light source 101 on the photocatalytic film 52, titanium (Ti) in titanium oxide contained in the photocatalytic film 52 reacts with water ($H_2O$) in the culture medium to form hydroxyl groups (—OH) on the surface of the photocatalytic film 52. Therefore, the irradiation of light from the light source 101 makes the surface of the photocatalytic film 52 hydrophilic. The degree of hydrophilicity of the photocatalytic film 52 surface varies depending on the light intensity of the light emitted from the light source 101.

When the photocatalytic film 52 surface is hydrophilic, the adhesiveness of cells to the photocatalytic film 52 surface is increased. In contrast, when the photocatalytic film 52 is hydrophobic, the adhesiveness of cells to the photocatalytic film 52 surface is decreased. Thus, the light intensity of the light emitted from the light source 101 is regulated by the light intensity regulator 102 to enable the control of the adhesiveness of cells to the photocatalytic film 52 surface.

As an indicator of the activity of cells cultured on the photocatalytic film 52 surface, the cell activity-measuring device 201 measures, for example, the proliferation rate of the cells. The cell activity-measuring device 201 is provided, for example, with a phase microscope disposed above the cell culture vessel 51 and an image analyzer for analyzing that image of cells on the cell culture vessel 51 obtained through the phase microscope and measuring the number of the cells. The cell activity-measuring device 201 calculates the proliferation rate of the cells based on the temporal change of the number of measured cells.

The association device 103 is electrically connected to the cell activity-measuring device 201 and the light intensity regulator 102. The association device 103 obtains data on the measured proliferation rate of the cells from the cell activity-measuring device 201. The association device 103 obtains from the light intensity regulator 102 data on the light intensity emitted from the light source 101 when the cells of which proliferation rate is measured by the cell activity-measuring device 201 are cultured. In addition, the association device 103 associates the data on the light intensity with the data on the proliferation rate of the cells.

The cell culture system according to the first embodiment further comprises an information storage device 104. The association device 103 stores the data on the proliferation rate of the cells associated with the data on the light intensity in the information storage device 104. In the information storage device 104, for example, a first proliferation rate $A_1$ of the cells in the case where light of a first light intensity $V_1$ is irradiated on the photocatalytic film 52, a second proliferation rate $A_2$ of the cells in the case where light of a second light intensity $V_2$ stronger than the first light intensity $V_1$ is irradiated thereon, a third proliferation rate $A_3$ of the cells in the case where light of a third light intensity $V_3$ stronger than the second light intensity $V_2$ is irradiated thereon, and the like are stored in table form as shown in FIG. 2.

The extraction device 105 shown in FIG. 1 extracts a value of the light intensity at which the fastest proliferation rate of the cells is obtained from the table shown in FIG. 2 stored in the information storage device 104. The extraction device 105 shown in FIG. 1 is electrically connected to the light intensity regulator 102. The light intensity regulator 102 receives the value of the light intensity at which the fastest proliferation rate of the cells is obtained from the extraction device 105. The light intensity regulator 102 further adjusts the light intensity of light emitted from the light source 101 to the value extracted by the extraction device 105.

The cell culture system according to the first embodiment further comprises an input device 312 and an output device 313. As the input device 312, a keyboard, and a pointing device such as a mouse can be used, for example. As the output device 313, a liquid crystal display, an apparatus for displaying an image such as a monitor, a printer, and the like can be used.

Figure 3:
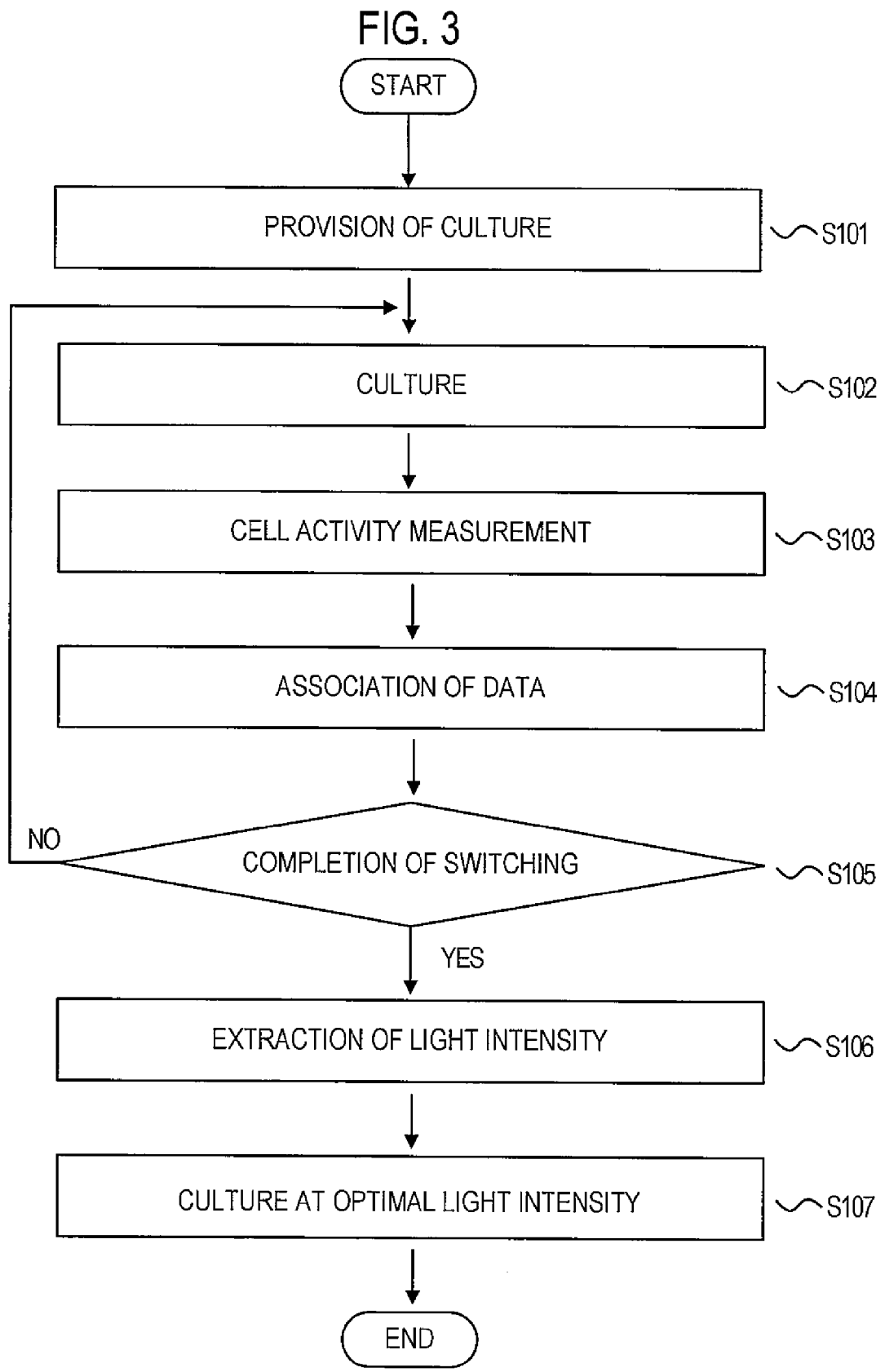
FIG. 3 is a flow chart depicting the cell culture method according to the first embodiment.

Next, the cell culture method according to the first embodiment is described using the flow chart shown in FIG. 3. Here, using "n" as a natural number, examples of irradiating the photocatalytic film 52 employing "n" types of light intensity are described.

(a) In step S101, the cell culture vessel 51 is provided which comprises the photocatalytic film 52 shown in FIG. 1. Next, a cell culture medium is placed in the cell culture vessel 51, and cells are seeded on the photocatalytic film 52. The cell culture vessel 51 on which the cells have been seeded is then disposed over the light source 101 in the cell culture system. In step S102, the light intensity regulator 102 regulates electric power supplied to the light source 101 so that it emits light having the first light intensity $V_1$. The cells are cultured on the photocatalytic film 52 for a predetermined period of time while irradiating the photocatalytic film 52 with the light having the first light intensity $V_1$.

(b) In step S103, the cell activity-measuring device 201 measures the first proliferation rate $A_1$ of the cells as an indicator of the activity of the cells cultured on the photocatalytic film 52 irradiated with light having the first light intensity $V_1$. In step S104, the association device 103 receives data on the first light intensity $V_1$ from the light intensity regulator 102 and receives data on the first proliferation rate $A_1$ of the cells from the cell activity-measuring device 201. Next, the association device 103 associates the data on the first proliferation rate $A_1$ of the cells with the data on the first light intensity $V_1$. The association device 103 then stores a data set of the associated first light intensity $V_1$ and first proliferation rate $A_1$ of the cells in the information storage device 104.

(c) In step S105, the light intensity regulator 102 determines whether the switching of the light intensity of light emitted from the light source 101 has been completed or not. When the switching thereof to a 2nd to "n"th light intensity $V_2$ to $V_n$ has not been completed, the light intensity regulator 102 regulates electric power supplied to light source 101 so that it emits light having the second light intensity, followed by return to step S102. Steps S102 to S105 are hereinafter repeated until the switching to the "n"th light intensity is completed. This results in the storage of data on the 1st to "n"th light intensity $V_1$ to $V_n$ and data on the 1st and "n"th proliferation rate $A_1$ to $A_n$ of the cells in the information storage device 104, as shown in FIG. 2, in the form that the $V_1$ to $V_n$ data are associated with the $A_1$ to $A_n$ data, respectively.

(d) In step S106, the extraction device 105 shown in FIG. 1 extracts a light intensity $V_M$ associated with the fastest proliferation rate $A_M$ among the data on the 1st to "n"th proliferation rate $A_1$ to $A_n$ of the cells stored in the information storage device 104. The extraction device 105 also outputs the extracted light intensity $V_M$ to the output device 313. In step S107, the light intensity regulator 102 receives the data on the extracted light intensity $V_M$ from the extraction device 105. Next, the light intensity regulator 102 regulates electric power supplied to the light source 101 so that it emits light having the extracted light intensity $V_M$. The cells are then cultured on the photocatalytic film 52 while irradiating the photocatalytic film 52 with the light having the light intensity $V_M$; after a predetermined period of time, the culture is terminated.

The cell activities indicated by the proliferation rate and the like of cells depend on the adhesiveness of the cells to a cell culture vessel. The cell culture system and cell culture method according to the first embodiment described above make it possible to vary the adhesiveness of cells to the photocatalytic film 52 provided in the cell culture vessel 51 depending on the light intensity of light irradiated on the photocatalytic film 52. In addition, the proliferation of the cells can be promoted with high efficiency by extracting a light intensity giving the fastest proliferation rate and thereafter culturing the cells on the photocatalytic film 52 while irradiating the photocatalytic film 52 with light having the extracted light intensity.

The example in which the cell activity-measuring device 201 comprises a phase microscope or the like has been described. However, the first embodiment is not intended to be limited thereto. For example, the cell activity-measuring device 201 may be a flow cytometer or the like. Here, the proliferation number of cells can be measured by measuring the number of cells peeled from a given area of the photocatalytic film 52 using the flow cytometer.

(Second Embodiment)

Figure 4:
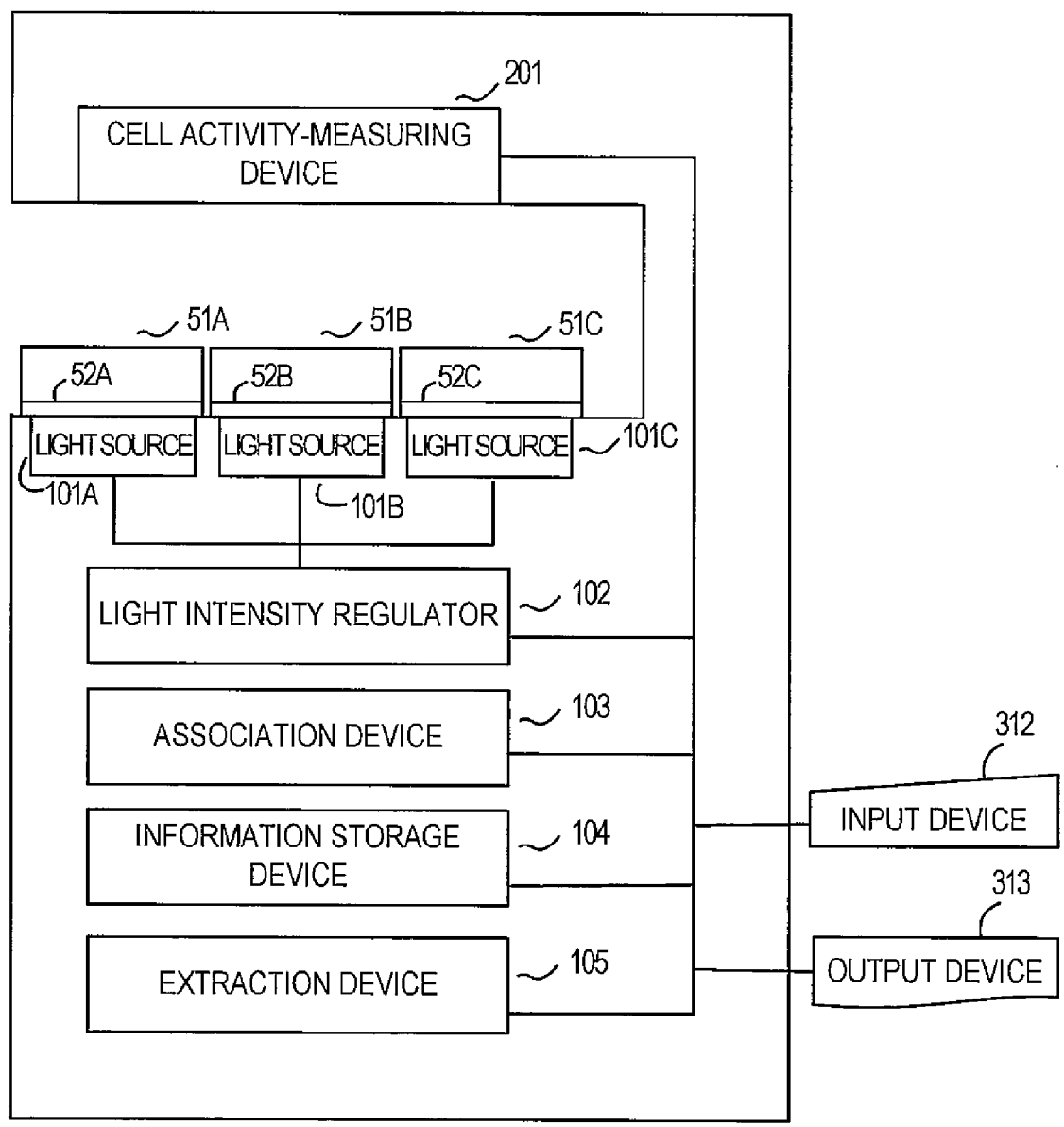
FIG. 4 is a schematic diagram of the cell culture system according to the second embodiment.

As shown in FIG. 4, the cell culture system according to the second embodiment comprises a plurality of light sources 101A, 101E and 101C. A light intensity regulator 102 supplies a different electric power to each of the plurality of light sources 1011, 101B and 101C. This allows each of the plurality of light sources 101A, 101B and 101C to emit light having a different intensity.

A plurality of cell culture vessels 51A, 51B and 51C are disposed over the plurality of light sources 101A, 101B and 101C. The plurality of cell culture vessels 51A, 51B and 51C comprise photocatalytic films 52A, 52B and 52C, respectively. The compositions of the photocatalytic films 52A, 52B and 52C are the same. Cells of the same line are seeded on the photocatalytic films 52A, 52B and 52C. The other components of the cell culture system according to the second embodiment are similar to those of the cell culture system according to the first embodiment.

The cell culture system according to the second embodiment makes it possible to obtain data on the activity of cells on the photocatalytic films 52A, 52B and 52C irradiated with light of different light intensities in parallel. Thus, data on the cell activity associated with the light intensity can be rapidly obtained.

(Third Embodiment)

Figure 5:
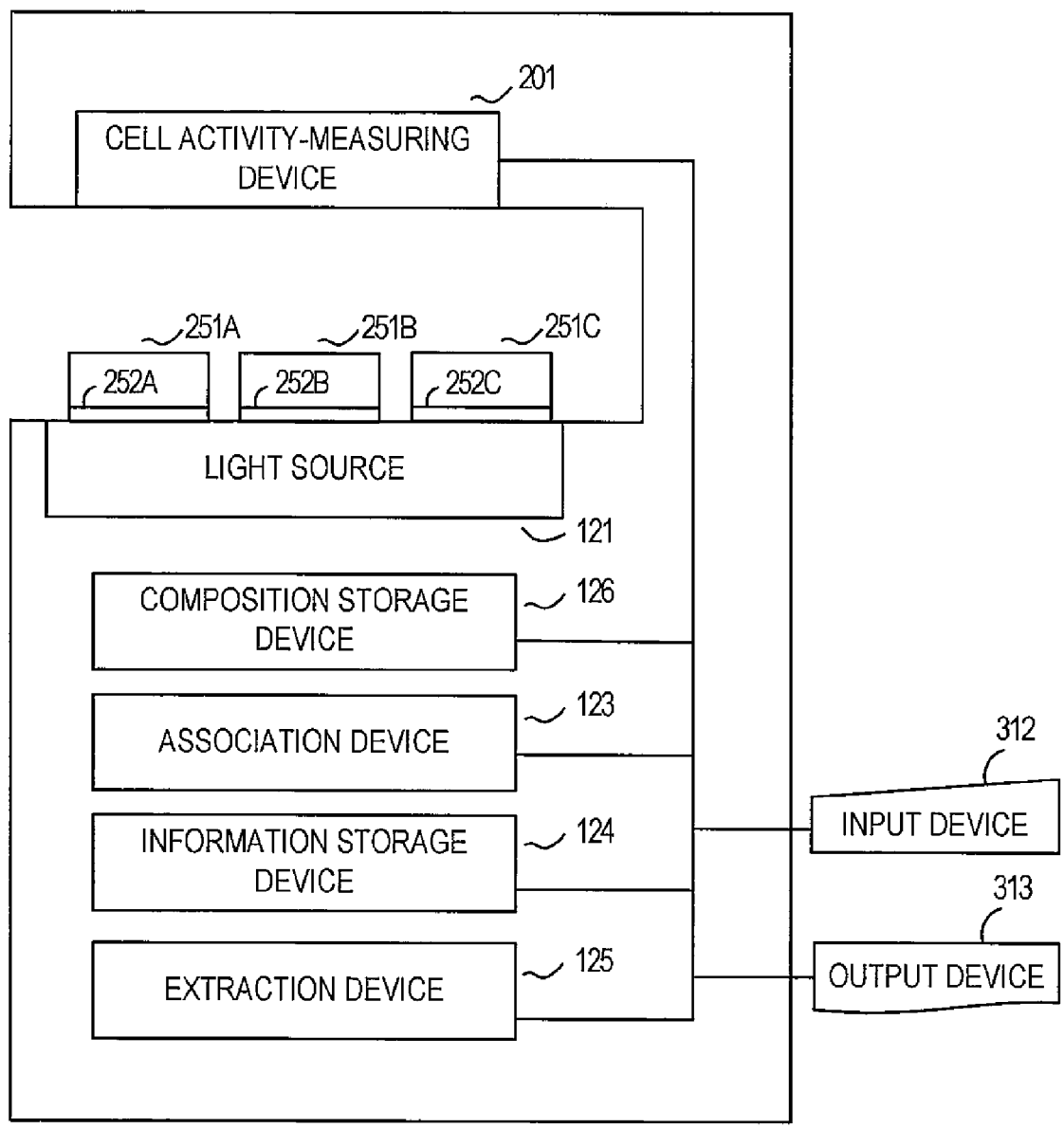
FIG. 5 is a schematic diagram of the cell culture system according to the third embodiment.

In the cell culture system shown in FIG. 5 according to the third embodiment, cell culture vessels 251A, 251B and 251C are disposed over a light source 121. The cell culture vessels 251A, 251B and 251C comprise photocatalytic films 252A, 252B and 252C, respectively. According to the third embodiment, the compositions of the photocatalytic films 252A, 252B and 252C are different. The cell culture system according to the third embodiment comprises a composition storage device 126. The composition $C_1$ of the photocatalytic film 252A, composition $C_2$ of the photocatalytic film 252B and composition $C_3$ of the photocatalytic film 252C inputted through an input device 312 are stored in the composition storage device 126.

The photocatalytic films 252A, 252B and 252C are irradiated with light under the same conditions emitted from the light source 121. A cell activity-measuring device 201 measures the proliferation rate of the cells as an indicator of the activity of cells cultured on the surface of each of the photocatalytic films 252A, 252B and 252C of differing compositions, for example.

An association device 123 according to the third embodiment is electrically connected to the cell activity-measuring device 201 and the composition storage device 126. The association device 123 obtains data on the measured proliferation rate of the cells from the cell activity-measuring device 201. The association device 123 also obtains data on the composition of each of the photocatalytic films 252A, 252B and 252C that are used when the cells of which proliferation rates are measured by the cell activity-measuring device 201 are cultured, from the composition storage device 126. In addition, the association device 123 associates the data on the proliferation rate of the cells with the data on the composition each of the photocatalytic films 252A, 252B and 252C.

The association device 123 stores, in an information storage device 124, the data on the proliferation rate of the cells associated with the data on the composition of each of the photocatalytic films 252A, 252B and 2520. In the information storage device 124, for example, a first proliferation rate $A_1$ of the cells with the composition $C_1$ of the photocatalytic film 252A, a second proliferation rate $A_2$ of the cells with the composition $C_2$ of the photocatalytic film 252B, a third proliferation rate $A_3$ of the cells with the composition $C_3$ of the photocatalytic film 252C and the like are stored in table form as shown in FIG. 6. The extraction device 125 shown in FIG. 5 extracts the composition of the photocatalytic film giving the fastest proliferation rate of the cells from the table shown in FIG. 6 stored in the information storage device 124.

Next, the cell culture method according to the third embodiment is described using the flow chart shown in FIG. 7.

(a) In step S121, the cell culture vessel 2511 comprising the photocatalytic film 252A consisting of the composition $C_1$, cell culture vessel 251B comprising the photocatalytic film 252B consisting of the composition $C_2$ and cell culture vessel 251C comprising the photocatalytic film 252C consisting of the composition $C_3$ shown in FIG. 5 are provided. Next, a cell culture medium is poured into the cell culture vessels 2511, 251B and 251C, and cells are seeded on the photocatalytic films 252A, 252B and 252C. The cell culture vessels 251A, 251B and 251C in which the cells are seeded are then disposed over the light source 121 in the cell culture system. In step S122, the cells are cultured on the photocatalytic films 252A, 252B and 252C for a predetermined period of time while irradiating light on the photocatalytic films 252A, 252B and 252C.

(b) In step S123, the cell activity-measuring device 201 measures the first proliferation rate $A_1$ of the cells cultured on the photocatalytic film 252A, the second proliferation rate $A_2$ of the cells cultured on the photocatalytic film 252B and the third proliferation rate $A_3$ of the cells cultured on the photocatalytic film 252C. In step S124, the association device 123 reads data on the compositions $C_1$, $C_2$ and $C_3$ of the photocatalytic films 252A, 252B and 2520, respectively from the composition storage device 126, and receives data on the first to third proliferation rates $A_1$, $A_2$ and $A_3$ of the cells from the cell activity-measuring device 201. Next, the association device 123 associates the data on the first proliferation rate $A_1$ of the cells with the data on the composition $C_1$, associates the data on the second proliferation rate $A_2$ of the cells with the data on the composition $C_2$ and associates the data on the third proliferation rate $A_3$ of the cells with the data on the composition $C_3$. As shown in FIG. 6, the association device 123 then stores, in the information storage device 124 shown in FIG. 5, sets of the associated data on the compositions $C_1$, $C_2$ and $C_3$ and the 1st to "n"th proliferation rates $A_1$ to $A_n$ of the cells, respectively.

(c) In step S126, the extraction device 125 extracts a composition $C_M$ associated with the fastest proliferation rate $A_M$ among the data on the 1st to "n"th proliferation rates $A_1$ to $A_n$ of the cells stored in the information storage device 124. The extraction device 125 also outputs the extracted composition $C_M$ to the output device 313. Then, in step S127, the cells are cultured on a photocatalytic film consisting of the composition $C_M$, and the culture is terminated after a predetermined period of time.

The adhesiveness of cells to the photocatalytic films 252A, 252B and 252C varies depending on the composition of the photocatalytic films 252A, 252B and 252C, respectively. According to the cell culture system and cell culture method in accordance with the third embodiment, a composition giving the fastest proliferation rate can be extracted from among the provided compositions of the photocatalytic films 252A, 252B or 252C, followed by culturing the cells on a photocatalytic film consisting of the extracted composition to promote the cell proliferation with high efficiency. The photocatalytic film consisting of the extracted composition can also be formed on a substrate to manufacture a cell culture vessel capable of promoting the cell proliferation with high efficiency.

(Other Embodiments)

The first to third embodiments have been described; however, from the disclosure, various alternative modes, embodiments, and operation technologies will become apparent to those skilled in the art. For example, although the proliferation rate of cells has been described as an indicator of the cell activity in the first to third embodiments, the indicator of the cell activity is not limited thereto. As an indicator of the cell activity, for example, the growth rate of cells, the amount of secreted material indicative of the cell activity, the gene expression level reflecting the cell activity, or the like may be measured using the cell activity-measuring device 201 shown in FIG. 1.

When the growth rate of cells is measured, a phase microscope or the like can be used as the cell activity-measuring device 201. When the amount of secreted material is measured, a device that can perform a cell membrane capacitance method, a quinacrine fluorescence method, a reverse hemolytic plaque assay, a cell blot assay, or the like may be used as the cell activity-measuring device 201. When the gene expression level is measured, a device that can perform a luciferase assay may be used as the cell activity-measuring device 201.

Titanium oxide in the photocatalytic film 52 may also be doped with nitrogen (N) ion, sulfur (S) ion, carbon (C) ion, fluorine (F) ion, or the like to enhance the reactivity to visible light.

Industrial Applicability

The cell culture system, cell culture method, cell culture vessel and method for manufacturing the cell culture vessel according to the present disclosure can be used in the pharma industry, cosmetic industry, food industry, and the like.

The invention claimed is:

1. A cell culture method comprising:
   emitting light of which light intensity can be regulated;
   preparing a cell incubator comprising a photocatalytic film consisting of titanium oxide and in which: a culture medium is injected; titanium in the titanium oxide reacts with water in the culture medium, by irradiated light, to form hydroxyl groups on the surface of the photocatalytic film; and the degree of hydrophilicity of the photocatalytic film surface varies depending on the light intensity of the light irradiated;
   culturing cells on a surface of the photocatalytic film consisting of titanium oxide whose degree of hydrophilicity varies depending on the light intensity;
   measuring the activity of cells cultured on the photocatalytic film irradiated with the light; and
   associating the light intensity with the activity of the cells.

2. The cell culture method of claim 1, further comprising extracting a value of the light intensity that maximizes the activity of the cells.

3. The cell culture method of claim 2, further comprising irradiating the photocatalytic film with light having the light intensity of the extracted value and culturing the cells on a surface of the photocatalytic film.

4. The cell culture method of claim 1, wherein the proliferation rate of the cells is measured in measuring the activity of the cells.

5. The cell culture method of claim 1, wherein the growth rate of the cells is measured in measuring the activity of the cells.

6. The cell culture method of claim 1, wherein the amount of secreted material indicative of the activity of the cells is measured in measuring the activity of the cells.

7. The cell culture method of claim 1, wherein the gene expression level indicative of the activity of the cells is measured in measuring the activity of the cells.

* * * * *

UNITED STATES PATENT AND TRADEMARK OFFICE
CERTIFICATE OF CORRECTION

Page 1 of 1

PATENT NO. : 9,080,138 B2
APPLICATION NO. : 12/665020
DATED : July 14, 2015
INVENTOR(S) : Kusuura It is certified that error appears in the above-identified patent and that said Letters Patent is hereby corrected as shown below:

Specification

In Column 6, Line 40, delete "101A, 101E and 101C." and insert -- 101A, 101B and 101C. --, therefor.

In Column 6, Line 42, delete "1011, 101B and 101C." and insert -- 101A, 101B and 101C. --, therefor.

In Column 7, Line 32, delete "film 252A, 252B and 2520," and insert -- film 252A, 252B and 252C, --, therefor.

In Column 7, Line 46, delete "vessel 2511" and insert -- vessel 251A --, therefor.

In Column 7, Lines 52-53, delete "vessels 2511, 251B and 251C," and insert -- vessels 251A, 251B and 251C, --, therefor.

In Column 8, Line 1, delete "252A, 252B, and 2520," and insert -- 252A, 252B, and 252C, --, therefor.

Signed and Sealed this
Twenty-ninth Day of December, 2015

Michelle K. Lee
*Director of the United States Patent and Trademark Office*